United States Patent

Babin et al.

Patent Number: 5,504,112

Date of Patent: Apr. 2, 1996

[54] PYRETHRINOID ESTERS

[75] Inventors: Didier Babin, Montigny; Marc Benoit, Roquevaire; Raphael Bouchet, Paris; Jean-Pierre Demoute, Neuilly Plaisance, all of France

[73] Assignee: Roussel Uclaf, France

[21] Appl. No.: 441,331

[22] Filed: May 15, 1995

Related U.S. Application Data

[63] Continuation of Ser. No. 280,798, Jul. 26, 1994, abandoned.

[30] Foreign Application Priority Data

Aug. 5, 1993 [FR] France .................. 93 09653

[51] Int. Cl.⁶ ........................................ A01N 53/00
[52] U.S. Cl. ................. 514/531; 560/124; 558/407; 558/434; 514/521
[58] Field of Search ............... 560/124; 558/407, 558/434; 514/531, 521

[56] References Cited

U.S. PATENT DOCUMENTS

| | | | |
|---|---|---|---|
| 3,673,215 | 6/1972 | Vollrath | 560/124 |
| 3,792,079 | 2/1974 | D'Orazio | 560/124 |
| 4,024,163 | 5/1977 | Elliott | 560/124 |
| 4,252,820 | 2/1981 | Lantzsch | 560/124 |
| 4,310,540 | 1/1982 | Lantzsch | 560/124 |
| 4,332,815 | 6/1982 | Engel | 560/124 |
| 4,385,070 | 5/1983 | Bentley | 560/124 |
| 4,879,302 | 11/1989 | Tessier | 560/124 |
| 4,939,172 | 7/1990 | Cadiergue | 560/124 |
| 5,336,670 | 8/1994 | Beniot | 560/124 |
| 5,420,159 | 5/1995 | Babin | 560/124 |

FOREIGN PATENT DOCUMENTS

| | | | |
|---|---|---|---|
| 61713 | 10/1982 | European Pat. Off. | 560/124 |
| 381563 | 8/1990 | European Pat. Off. | 560/124 |
| 3005722 | 8/1981 | Germany. | |
| 3900275 | 7/1990 | Germany. | |
| 58-121246 | 7/1983 | Japan | 560/124 |
| 2088369 | 6/1982 | United Kingdom | 560/124 |

OTHER PUBLICATIONS

Norton, Botyu–Kagaku, 41, pp. 1–7 (1976).

*Primary Examiner*—Michael L. Shippen
*Attorney, Agent, or Firm*—Bierman and Muserlian

[57] ABSTRACT

A compound in all possible stereoisomeric forms and their mixtures of the formula

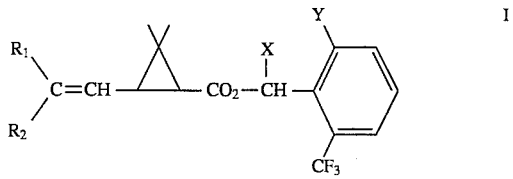

wherein X is selected from the group consisting of hydrogen, —CN, alkyl, alkenyl and alkynyl of up to 4 carbon atoms and aralkynyl of up to 10 carbon atoms, Y is selected from the group consisting of halogen, —$CF_3$, —$CH_2F$ and —$CHF_2$ and $R_1$ is hydrogen and $R_2$ is halogen or $R_1$ and $R_2$ are —$CF_3$ or $R_1$ and $R_2$ are individually halogen.

5 Claims, No Drawings

PYRETHRINOID ESTERS

This application is a continuation of U.S. patent application Ser. No. 280,798 filed Jul. 26, 1994, now abandoned.

OBJECTS OF THE INVENTION

It is an object of the invention to provide the novel esters of formula I and a process and intermediate for their preparation.

It is another object of the invention to provide novel pesticidal compositions and a novel method of combatting pests, especially insects.

These and other objects and advantages of the invention will become obvious from the following detailed description.

THE INVENTION

The novel compounds of the invention are all possible stereoisomeric forms and their mixtures of the formula

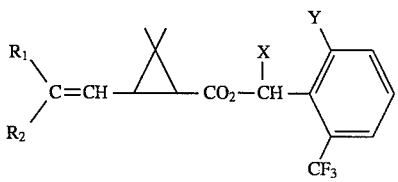

wherein X is selected from the group consisting of hydrogen, —CN, alkyl, alkenyl and alkynyl of up to 4 carbon atoms and aralkynyl of up to 10 carbon atoms, Y is selected from the group consisting of halogen, —$CF_3$, —$CH_2F$ and —$CHF_2$ and $R_1$ is hydrogen and $R_2$ is halogen or $R_1$ and $R_2$ are —$CF_3$ or $R_1$ and $R_2$ are individually halogen.

When X is alkyl, it is preferably methyl or ethyl and when X is alkenyl or alkynyl, it is preferably vinyl or ethynyl. When Y is halogen, it is preferably fluorine, bromine or chlorine.

Among the preferred compounds of formula I are those wherein the cyclopropane moiety has 1R, cis configuration, those wherein X is hydrogen, those wherein Y is —$CF_3$, or F and those wherein $R_1$ and $R_2$ are different halogens such as $R_1$ is fluorine and $R_2$ is chlorine or $R_1$ and $R_2$ are —$CF_3$. The most preferred compound is 2,6-bis-trifluoromethyl-benzyl 1R, cis 2, 2-dimethyl-3-(2-fluoro-2-chloro-vinyl)-cyclopropane carboxylate.

The process of the invention for the preparation of the compounds of formula I comprises reacting an acid of the formula

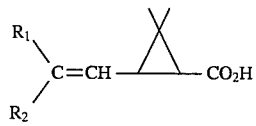

wherein $R_1$ and $R_2$ are defined above or a functional derivative thereof with an alcohol of the formula

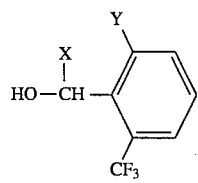

wherein X and Y are defined above or a functional derivative thereof to form the corresponding ester of formula I.

The functional derivative of the acid used is preferably an acid chloride. When the acid of formula II is reacted with the alcohol of formula III, the operation is preferably carried out in the presence of dicyclohexylcarbodiimide.

The alcohols of formula III are products known generally and 2-fluoro-6-(trifluoromethyl)-benzyl alcohol is a commercial product. 2,6-bis-trifluoromethyl-benzyl alcohol is a novel product whose preparation is given in the experimental part.

The acids of formula II used as starting products are in general known products used in the synthesis of pyrethrinoid compounds described in French Patent No. 2,185,612, European Patent Application No. 0,378,026 and No. 0,381,563 and in U.S. Pat. No. 4,332,815.

1R, cis 2,2-dimethyl-3-(2,2-bis-trifluoromethyl-vinyl)-cyclopropane carboxylic acid can be prepared as indicated in the experimental part by reacting a compound of the formula:

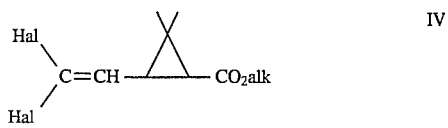

wherein Hal is halogen, preferably bromine and alk is alkyl of up to 4 carbon atoms with $CF_3$ ions and fluoride ions in the presence of copper salts, for example with trifluoromethyl trimethylsilane and potassium fluoride in the presence of copper salts to obtain a compound of the formula:

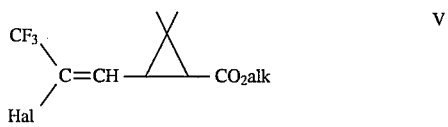

which is subjected to the action of $CF_3$ ions and fluoride ions for example trifluoromethyl trimethylsilane and potassium fluoride in the presence of a copper salt, to obtain a compound of the formula:

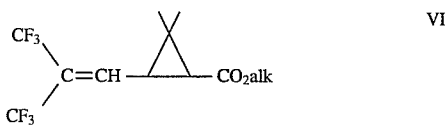

which is subjected to the action of a hydrolysis agent of the ester function to obtain the desired acid.

A copper halide or a copper cyanide can be used as the copper salt and the hydrolysis agent is preferably an acid hydrolysis agent.

The novel pesticidal compositions of the invention are comprised of a pesticidally effective amount of at least one compound of formula I and an inert carrier. The compositions of the invention are useful for combating parasites of vegetation, parasites of premises and parasites of warm-blooded animals and can be used to combat parasitic insects, nematodes and acaridae of vegetation and of animals. They are particularly useful for combating parasites of vegetation, parasites of premises and parasites of warm-blooded animals.

The compositions can also be used to combat insects and other parasites of the soil, for example Coleoptera such as Diabrotica, click beetles and May beetle grubs, Myriapoda such as scutigeridae and blanjules, Diptera such as cecydomia and Lepidoptera such as owlet moths. They are used at doses between 10 g and 300 g of active ingredient per hectare.

The compositions can also be used to combat insects in premises, to combat particularly flies, mosquitoes and cockroaches.

All of these properties make the compositions which correspond perfectly to the requirements of the modern agrochemical industry useful for crops to be protected while preserving the environment. The compositions can also be used to combat parasitic acaridae and nematodes of vegetation.

The compositions can also be used to combat parasitic acaridae of animals, to combat for example ticks and particularly ticks of the *boophilus* species, those of the *hyalomnia* species, those of the *amblyomnia* species and those of the *rhipicephalus* species or to combat all types of mites and particularly the sarcoptic mite, the psoroptic mite and the chorioptic mite.

More particularly, the insecticide compositions defined above are intended for combating Diabrotica and other parasites of the soil.

These compositions are prepared by the usual processes of the agrochemical industry or the veterinary industry or the industry for products intended for animal nutrition. The compositions intended for agricultural use and use in premises, can optionally have added to them one or more other pesticide agents. These compositions can appear in the form of powders, granules, suspensions, emulsions, solutions, aerosol solutions, combustible strips, baits or other preparations usually employed for the use of these types of compounds.

In addition to the active ingredient, these compositions contain generally a vehicle and/or a nonionic surface active agent, to ensure a uniform dispersion of the substances of the mixture. The vehicle used can be a liquid such as water, alcohol, hydrocarbons or other organic solvents, a mineral, animal or vegetable oil, a powder such as talc, clays, silicates, kieselguhr or a combustible solid. The insecticide compositions of the invention preferably contain from 0.005% to 10% by weight of active ingredient.

According to an advantageous operating method for use in premises, the compositions are used in the form of fumigant compositions and can then advantageously be constituted for the non-active part by a combustible insecticide coil, or also by an incombustible fibrous substrate. In this last case, the fumigant obtained after incorporation of the active ingredient is placed on a heating apparatus such as an electric vaporizer.

In the case where an insecticide coil is used, the inert support can be pyrethrum marc compound, Tabu powder (or Machilus Thumbergii leaf powder), pyrethrum stem powder, cedar leaf powder, sawdust (such as pine sawdust) starch and coconut shell powder. The dose of active ingredient can then be, for example, 0.03 to 1% by weight. In the case where an incombustible fibrous support is used, the dose of active ingredient can then be 0.03 to 95% by weight.

The compositions of the invention for use in premises can also be obtained by preparing a sprayable oil based on the active ingredient, this oil soaking the wick of a lamp and then being set alight. The concentration of active ingredient incorporated in the oil is, preferably, 0.03 to 95% by weight.

Also, acaricide and nematicide compositions of at least one of the products of formula I as active ingredient are useful.

The insecticide compositions of the invention as acaricide and nematicide compositions can optionally have added to them one or more other pesticide agents and can be presented particularly in the form of powders, granules, suspensions, emulsions, solutions.

For acaricide use, wettable powders for foliar spraying containing 1 to 80% by weight of active ingredient or liquids for foliar spraying containing 1 to 500 g/l of active ingredient, are preferably used. Powders can also be used for foliar dustings containing 0.05 to 3% of active ingredient. For nematicide use, liquids for soil treatment are preferably used containing 300 to 500 g/l of active ingredient. The acaricide and nematicide compositions are used preferably at doses comprised between 1 and 100 g of active ingredient per hectare.

To enhance the biological activity of the compositions, they can be added to standard synergists used in such cases, such as 1-(2,5,8-trioxadodecyl) -2-propyl-4,5-methylenedioxy benzene (or piperonyl butoxide) or N-(2-ethyl-heptyl)-bicyclo-[2,2-1]-5-heptene-2,3-dicarboximide, or piperonyl-bis-2-(2'-n-butoxy-ethoxy) ethylacetal (or tropital).

The compounds of formula I have an excellent general tolerance, and therefore are useful for combating illnesses caused by ticks and mites in man and in animals, particularly to combat lice as a preventive or curative and to combat scabies. The compositions can be administered externally, by spraying, by shampooing, by bathing or painting on.

The compositions for veterinary use can also be administered by painting on the dorsal spine by the so-called "pour-on" method.

The compositions of the invention can be used as biocides or as growth regulators. Combinations endowed with insecticide, acaricide or nematicide activity include at least one of compound of formula I and at least one of the pyrethrinoid esters selected from the group consisting of the esters of allethrone, of 3,4,5,6-tetrahydrophthalimidomethyl alcohol, of 5-benzyl-3-furyl methyl alcohol, of 3-phenoxybenzyl alcohol and of alpha-cyano-3-phenoxybenzyl alcohol with chrysanthemic acids, by the esters of 5-benzyl-3-furyl methyl alcohol with 2,2-dimethyl-3-(2-oxo-3-tetrahydrothiophenylidenemethyl) -cyclopropane-carboxylic acids, by the esters of 3-phenoxybenzyl alcohol and of alpha-cyano-3phenoxybenzyl alcohol with 2,2-dimethyl-3-(2,2-dichlorovinyl)cyclopropanecarboxylic acids, by the esters of alpha-cyano-3-phenoxy-benzyl alcohol with 2,2-dimethyl-3-(2,2-dibromovinyl)cyclopropanecarboxylic acids, by the esters of 3-phenoxybenzyl alcohol with 2-parachlorophenyl-2-isopropyl acetic acids, by the esters of allethrolone, of 3,4,5,6-tetrahydrophthalimidomethyl alcohol, of 5-benzyl-3-furyl methyl alcohol, of 3-phenoxybenzyl alcohol and of alpha-cyano-3-phenoxybenzyl alcohol with 2,2-dimethyl-3 -(1,2,2,2-tetrahaloethyl)-cyclopropane-carboxylic acids, in which "halo" is fluorine, chlorine or bromine, it being understood that the compounds of formula I can exist in all their possible stereoisomeric forms as well as the acid and alcohol copulas of the above pyrethrinoid esters.

The novel method of the invention for combatting pests, particularly insects, comprises contacting the pests, preferably insects, with a pesticidally effective amount of at least one compound of formula I.

In the following examples, there are described several preferred embodiments to illustrate the invention. However, it is to be understood that the invention is not intended to be limited to the specific embodiments.

EXAMPLE 1

1: 2,6-bis-trifluoromethyl-benzyl (1R,cis)-2,2-dimethyl-3-(2-fluoro-2-chloro-vinyl) -cyclopropane-carboxylate A solution of 0.43 g of dicyclohexyl-carbodiimide (DCC), 10 mg of 4-dimethylamino-pyridine (DMAP) and 10 ml of methylene chloride was added dropwise at 0° C. to a solution of 0.4 g of (1R,cis) 2,2-dimethyl-3 -(2-fluoro-2-chloro)-cyclopropanecarboxylic acid, 0.49 g of 2,6-bis-trifluoromethyl-benzyl alcohol and 10 ml of methylene chloride. The reaction mixture was allowed to return to ambient temperature, followed by evaporating to dryness and chromatographing on silica and eluting with a hexane-ethyl acetate mixture to obtain 0.67 g of the desired product.

| Analysis: | calculated | found |
|---|---|---|
| C | 48.76% | 49.0% |
| H | 3.37% | 3.3% |
| Cl | 8.46% | 8.8% |
| F | 31.76% | 31.6% |

| NMR CDCl$_3$ ppm | | |
|---|---|---|
| 5.35 (dd, J=10–29) | CH=ethylenic | E |
| 5.75 (dd, J=8.5–10) | CH=ethylenic | Z |
| 2.06 (m) | } H$_3$ of the cyclopropane | |
| 1.81 (m) | | |
| 1.19 (s) | } H of the twinned methyls | |
| 1.21 (s) | | |
| 1.23 (s) | | |
| 1.75 | H$_1$ | |

By using the appropriate acids and alcohols, the following products were prepared:

EXAMPLE 2

2,6-bis-trifluoromethyl-benzyl (1R,cis)-2,2-dimethyl-3-(2,2-dichlorovinyl)-cyclopropane-carboxylate

| Analysis: | calculated | found |
|---|---|---|
| C | 46.9% | 47.1% |
| H | 3.2% | 3.2% |
| Cl | 16.3% | 16.2% |
| F | 26.2% | 25.8% |

| NMR: CDCl$_3$ ppm | |
|---|---|
| 1.22 (s) | } twinned CH$_3$'s |
| 1.25 (s) | |
| 1.81 | (d, J=8.5) H$_1$ |
| 2.03 | H$_3$ |
| 5.36 | CH$_2$ in alpha position of the CO$_2$ |
| 6.28 (d) | H of the double bond |
| 7.65 (t) | aromatic H$_4$ |
| 7.97 (d)2H | aromatic H$_3$ and H$_5$ |

EXAMPLE 3

2,6-bis-trifluoromethyl-benzyl (1R,cis)-2,2-dimethyl-3-(2,2-difluoro-vinyl)-cyclopropane-carboxylate.

| Analysis: | calculated | found |
|---|---|---|
| C | 50.76% | 50.6% |
| H | 3.5% | 3.5% |
| F | 37.78% | 37.3–37.4% |

| NMR: CDCl$_3$ ppm | |
|---|---|
| 1.19 (s) | } the twinned methyls |
| 1.22 (s) | |
| 1.68 (d, J=8.5) | } H$_1$ and H$_3$ of the cyclopropane |
| 1.83 (m) | |
| 4.67 (ddd, J=2–9.5–25.5) | ethylenic H |
| 7.64 (t, J=8) | aromatic H's in para position |
| 7.96 (d, J=8) | aromatic H's in meta position |

EXAMPLE 4

2,6-bis-trifluoromethyl-benzyl (1R, cis)-2,2-dimethyl-3-(2,2-dibromovinyl)-cyclopropane-carboxylate.

| Analysis: | calculated | found |
|---|---|---|
| C | 38.95% | 39% |
| F | 21.75% | 21.9% |
| H | 2.69% | 2.7% |
| Br | 30.49% | 30.4% |

| NMR: CDCl$_3$ ppm | |
|---|---|
| 1.21–1.28 (d) | H of the twinned CH$_3$'s |
| 1.91–1.98 (t) | H in position 3 of the cyclopropane |
| 1.2–1.83 (d) | H in position 1 of the cyclopropane |
| 6.78–6.81 (d) | vinyl H's |
| 5.2–5.5 | H of the CH$_2$ in alpha position of the CO$_2$ |
| 7.65 (s) | H in para position of the phenyl |
| 7.94—7.94 (d) | H in meta position of the phenyl |

EXAMPLE 5

2,6-bis-trifluoromethyl-benzyl (1R, cis)-2,2-dimethyl-3-[2,2-bis-trifluoromethyl-vinyl]-cyclopropane-carboxylate

| Analysis: | calculated | found |
|---|---|---|
| C | 45.43% | 45.1% |
| H | 2.8% | 2.7% |
| F | 45.38% | 44.0% |

| NMR: CDCl$_3$ ppm | |
|---|---|
| 1.27 (s), 1.32 (s) | H of the twinned CH$_3$'s |
| 2.05 (d, J=8) | H$_1$ |
| 2.19 (m) | H$_3$ |
| 5.30–5.46 | H of the CH$_2$ in alpha position of the CO$_2$ |
| 7.22 (dl) J=10.5 | ethylenic H |

EXAMPLE 6

2-fluoro-6-trifluoromethyl-benzyl (1R,cis)-2,2-dimethyl-3-(2,2-dichlorovinyl)-cyclopropane-carboxylate.
TLC: hexane-ethyl acetate 8-2 rf=0.3.
PREPARATION 1: 2,6-bis-trifluoromethyl-benzyl alcohol STAGE A: methyl 2,6-bis-trifluoromethyl-benzoate.

A solution of 6 g of 2,6-bis-trifluoromethyl-benzoic acid, 60 ml of tetrahydrofuran and 11.58 ml of a 2N sodium hydroxide solution was stirred for 30 minutes at 20° C. and after the reaction medium was cooled to 0° C., 4.26 ml of dimethyl sulfate were added. The mixture was stirred for 1 hour at 20° C. and another 2.1 ml of dimethyl sulfate were added. The reaction mixture was stirred for 24 hours at 20° C. and was then poured into an aqueous solution of sodium bicarbonate, extracted with isopropyl ether, then with ethyl acetate, dried, filtered, rinsed and brought to dryness. After chromatographing on silica (eluant hexane-ethyl acetate (9-1)), 5.59 g of the desired product were obtained.

STAGE B: 2,6-bis-trifluoromethyl-benzyl alcohol.

58 ml of a 1.2M solution of diisobutylaluminium hydride (DIBAH) were added at 0° C. to a solution of 5.59 g of the product of Stage A and 60 ml of toluene. The temperature was allowed to return to 20° C. and the reaction mixture was stirred for 4 hours, then poured into a molar solution of potassium and sodium double tartrate and extracted with isopropyl ether. The aqueous phase was saturated with sodium chloride, followed by extraction with ethyl acetate, drying, filtering, rinsing and bringing to dryness to obtain after chromatography on silica (eluant: hexane-ethyl acetate (9-1)), 4.72 g of the desired product.

PREPARATION 2: (R,cis)-2,2-dimethyl-3-[2,2-bis-trifluoromethylvinyl] -cyclopropane-carboxylic acid STAGE A: 1,1-dimethyl-ethyl (1R,cis)-2,2-dimethyl-3-(2-bromo-2-trifluoromethyl) -vinyl-cyclopropane-carboxylate.

A solution of 80 g of 1,1-dimethyl-ethyl (1R,cis)-2,2-dimethyl -3-(2,2-dibromovinyl)-cyclopropane-carboxylate, 22,3 g of potassium fluoride, 68.8 g of copper iodide, 63 ml of hexamethyl phosphotriamide (HMPT) and 100 ml of dimethylformamide was heated to 50° C. and 47 ml of trifluoromethyltrimethylsilane were introduced at 50° C. The reaction mixture was stirred at 80° C. for 8 hours and was then poured into water. 500 ml of isopropyl ether were added followed by filtering. The precipitate was rinsed with isopropyl ether and the ethereal phase was washed with water. The solvent was evaporated and chromatography was carried out on silica eluting with a flugene, dichloroethane 95-5 mixture to obtain the desired product.

STAGE B: 1,1-dimethyl-ethyl (1R,cis)-2,2-dimethyl-3-[2,2-bis-trifluoromethyl -vinyl]-cyclopropane-carboxylate.

A solution of 5 g of the product of Stage A, 2.16 g of potassium fluoride, 8.16 g of copper iodide, 7.5 ml of hexamethyl phosphotriamide and 50 ml of dimethylformamide was heated to 50° C. and 5.3 ml of trifluoromethyltrimethylsilane was introduced. The reaction medium was heated at 80° C. for 24 hours and 3 ml of trifluoromethyltrimethylsilane, 24 g of potassium fluoride and 4 g of copper iodide were added. The mixture was stirred for 24 hours at 80° C. and then was poured into distilled water. 50 ml of isopropyl ether were added, followed by filtering and rinsing with isopropyl ether. The ethereal phases were washed with water and the solvent was evaporated. The residue was chromatographed eluting with a flugene-1,2-dichloroethane 95-5 mixture to obtain 1 g of the expected product.

| NMR: CDCl$_3$ ppm | |
| --- | --- |
| 1.2–1.29 (d) | H of the twinned methyls |
| 7.24–7.27 (d) | vinyl H |
| 1.96–1.98 (d) | H in position 1 of the cyclopropane |
| 2.05–2.15 (t) | H in position 3 of the cyclopropane |
| 1.44 (s) | H of the terbutyls |

STAGE C: (1R,cis)-2,2-dimethyl-3-[2,2-bis-trifluoromethyl-vinyl-cyclopropane-carboxylic acid.

1.7 g of trifluoroacetic acid were introduced at 0° C. into a solution of 1 g of the product of Stage B and 8 ml of methylene chloride. The temperature was allowed to rise to 20° C. and the mixture was stirred for 10 hours. The solvent was evaporated by entraining the excess trifluoroacetic acid with toluene to obtain 0.6 g of the desired product.

| NMR: CDCl$_3$ ppm | |
| --- | --- |
| 1.32–1.34 (d) | H of the twinned methyls |
| 7.15–7.2 (d) | vinyl H |
| 2.08–2.1 (d) | H in position 1 of the cyclopropane |
| 2.21–2.32 (t) | H in position 3 of the cyclopropane |

EXAMPLE 7

Preparation of a soluble concentrate

A homogeneous mixture was prepared containing 0.25 g of the Product of Example 1, 1.00 g of Piperonyl butoxide, 0.25 of Tween 80, 0.1 g of Topanol A and 98.4 g of Water.

EXAMPLE 8

Preparation of an emulsifiable concentrate

The following were intimately mixed together:

Product of Example 1 : 0.015 g
Piperonyl butoxide 0.5 g
Topanol A : 0.1 g
Tween 80 : 3.5 g
Xylene : 95.885 g

BIOLOGICAL STUDY

A—Activity on Diabrotica

The test insects were final-stage larvae of Diabrotica and a 9 cm diameter disc of filter paper, placed at the bottom of a Petri dish was treated with 2 ml of an acetone solution of the test product. After drying, 15 larvae per dose were deposited and the mortality check was carried out 24 hours after treatment. Starting from a dose of 1 ppm, the products of the invention have a good activity.

Various modifications of the products and method of the invention may be made without departing from the spirit or scope thereof and it is to be understood that the invention is intended to be limited only as defined in the appended claims.

What we claim is:

1. A compound in all possible stereoisomeric forms and their mixtures of the formula

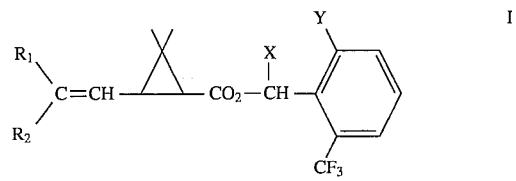

wherein X is hydrogen, Y is —CF$_3$, R$_1$ is fluorine and R$_2$ is chlorine.

2. A compound of claim 1 wherein the cyclopropane moiety has 1R, cis structure.

3. An insecticidal composition comprising an insecticidally effective amount of a compound of claim 1 and an inert carrier.

4. A composition of claim 3 also containing at least one of the pyrethrinoid esters selected from the group consisting of the esters of allethrone, of 3,4,5,6-tetrahydrophthalimidomethyl alcohol, of 5-benzyl-3-furyl methyl alcohol, of 3-phenoxybenzyl alcohol with chrysanthemic acids, by the esters of 5-benzyl-3-furyl methyl alcohol with 2,3-dimethyl-3-(2-oxo-3-tetrahydrophthalimidomethyl) -cyclopropane-carboxylic acids, by the esters of 3-phenoxybenzyl alcohol and of alpha-cyano-3-phenoxybenzyl alcohol with 2,2-dimethyl-3-(2,2-dichlorovinyl)cyclopropanecarboxylic acids, by the esters of alpha-cyano-3-phenoxy-benzyl alcohol with 2,2-dimethyl-3-(2,2-dibromovinyl)cyclopropanecarboxylic acids, by the esters of 3-phenoxybenzyl alcohol with 2-parachlorophenyl-2-isopropyl acetic acids, by the esters of allethrolone, of 3,4,5,6-tetrahydrophthalimidomethyl alcohol and of alpha-cyano-3-phenoxybenzyl alcohol with 2,2-dimethyl-3-(1,2,2,2-tetrahaloethyl) -cyclopropane-carboxylicacids, in which "halo" represents a fluorine, chlorine or bromine atom, it being understood that the compounds can exist in all their possible stereoisomeric forms.

5. A method of combatting insects comprising contacting insects with an insecticidally effective amount of a compound of claim 1.

* * * * *